(12) United States Patent
Zunker (10) Patent No.: US 6,969,380 B1
(45) Date of Patent: Nov. 29, 2005

(54) URINARY INCONTINENCE DEVICE AND METHOD OF MAKING SAME

(75) Inventor: MaryAnn Zunker, Oshkosh, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1060 days.

(21) Appl. No.: 09/675,459

(22) Filed: Sep. 28, 2000

(51) Int. Cl.$^7$ .......................... A61M 31/00; A61F 2/00
(52) U.S. Cl. ........................... 604/517; 600/29
(58) Field of Search ............. 604/385.18, 904, 604/517; 600/29–31

(56) References Cited

U.S. PATENT DOCUMENTS

| | | | |
|---|---|---|---|
| 2,938,519 A | 5/1960 | Marco |
| 3,646,929 A | 3/1972 | Bonnar |
| 4,019,498 A | 4/1977 | Hawtrey et al. |
| 4,139,006 A | 2/1979 | Corey |
| 4,920,986 A | 5/1990 | Biswas |
| 5,007,894 A | 4/1991 | Enhorning |
| 5,036,867 A | 8/1991 | Biswas |
| 5,045,079 A | 9/1991 | West |
| 5,386,836 A | 2/1995 | Biswas |
| 5,609,559 A | 3/1997 | Weitzner |
| 5,609,586 A | 3/1997 | Zadini et al. |
| 5,618,256 A | 4/1997 | Reimer et al. |
| 5,659,934 A | 8/1997 | Jessup et al. |
| 5,755,906 A | 5/1998 | Achter et al. |
| 5,785,640 A | 7/1998 | Kresch et al. |
| 5,795,346 A | 8/1998 | Achter et al. |
| 5,816,248 A | 10/1998 | Anderson et al. |
| 6,039,716 A | 3/2000 | Jessup et al. |
| 6,039,828 A | 3/2000 | Achter et al. |
| 6,090,038 A | 7/2000 | Zunker et al. |
| 6,090,098 A | 7/2000 | Zunker et al. |
| 6,095,998 A | 8/2000 | Osborn, III et al. |
| 6,142,928 A | 11/2000 | Zunker et al. |

FOREIGN PATENT DOCUMENTS

| | | |
|---|---|---|
| EP | 0 460 807 A2 | 12/1991 |
| EP | 0 264 258 B1 | 4/1992 |
| EP | 0 498 912 A1 | 8/1992 |
| EP | 0 363 421 B2 | 10/1995 |
| EP | 0 714 271 B1 | 5/1998 |
| WO | WO 88/10106 | 12/1988 |
| WO | WO 98/06365 | 2/1998 |
| WO | WO 00/36996 | 6/2000 |
| WO | WO 00/37012 | 6/2000 |
| WO | WO 00/37013 | 6/2000 |

OTHER PUBLICATIONS

U.S. Appl. No. 09/675,458, "Incontinence Insert Applicators And Methods For Their Use," filed Sep. 28, 2000.
U.S. Appl. No. 09/675,460, "Resilient Incontinence Insert And A Method Of Making The Same," filed Sep. 28, 2000.

*Primary Examiner*—Larry I. Schwartz
*Assistant Examiner*—C. Lynne Anderson
(74) *Attorney, Agent, or Firm*—Brinks Hofer Gilson & Lione; G. Peter Nichols (57) ABSTRACT

A urinary incontinence device for reducing the occurrence and/or severity of female urinary incontinence. The urinary incontinence includes a non-absorbent core structure and a resilient member having a generally trapezoidal shaped profile. The resilient member is adapted to expand the urinary incontinence device within a vagina, while also providing a soft tip for the facilitating the insertion of the device.

17 Claims, 8 Drawing Sheets

URINARY INCONTINENCE DEVICE AND METHOD OF MAKING SAME

FIELD OF THE INVENTION

The present invention relates to a urinary incontinence device and a method of making the device. More specifically, this invention relates to a non-absorbent urinary incontinence device which is designed to be placed inside a vagina for providing support to the urethra to prevent the involuntary urine loss commonly associated with stress urinary incontinence.

BACKGROUND

Some women, especially women who have given birth to one or more children, and older women, can experience incidences of involuntary urine loss due to stress urinary incontinence or combined stress and urge incontinence. A sneeze or cough can increase the intra-abdominal pressure impinging on a persons bladder and cause the involuntary release of urine. The frequency and severity of such urine loss can increase as the muscles and tissues near the urethrovaginal myofascial area grow weaker. It has also been recognized that the urinary sphincter muscle, which is located at the upper end of the urethra adjacent to the bladder, works well at sealing off the passing of urine from the bladder to the urethra when it has a round or circular cross-sectional configuration. However, when this passageway becomes distorted into a cross-sectional configuration having more of an elliptical or oval appearance, the sphincter muscle can not close properly, therefore, the tendency for involuntary urine loss increases. As the world's female population ages, there is an ever increasing need for a non-surgical procedure to reduce the involuntary urine loss commonly associated with "stress urinary incontinence." Today, there are a number of products available for this purpose. Essentially all of these products can only be purchased with a prescription and they need to be physically inserted and/or adjusted by a medical doctor or a nurse practitioner in order to perform correctly.

In view of the general lack of commercially available non-prescription urinary incontinence devices, it is recognized that there is a need for an effective urinary incontinence device which can be purchased without a prescription. There is also a need for a urinary incontinence device which is more user friendly and can be managed by the consumer without the intervention of a medical practitioner. Furthermore, there is a need for a urinary incontinence device which is easy for women to insert into and remove from their bodies, be more comfortable to wear and provide psychological and realistic assurance that it is capable of properly performing over an extended period of time.

SUMMARY

In one aspect of the invention, a urinary incontinence includes a resilient member having a generally trapezoidal profile, and an elongated non-absorbent core structure having a first end portion and a second end portion. The core structure is folded upon itself such that the first and second end portions are aligned substantially parallel to one another and the core structure contains at least two folds therebetween to form a generally M-shaped profile. The least two folds includes a first fold adjacent the first end portion and a second fold adjacent the second end portion. The resilient member is in contact with the core structure and positioned between the first fold and the second fold.

In another aspect of the invention, a urinary incontinence device includes a resilient member having a profile of two generally parallel sides connected by two generally non-parallel sides, wherein a shorter side of the two generally parallel sides forms an obtuse angle with each of the two generally non-parallel sides. The device also includes an elongated non-absorbent core structure having a first end portion, a second end portion, and a connecting portion between the first end portion and the second end portion. The core structure is folded such that the first and second end portions are aligned substantially parallel. The shorter side of the resilient member is in contact with the connecting portion, and the connecting portion is folded such that a first and second segment of the connecting portion is substantially aligned with and adjacent each of the two generally non-parallel sides of the resilient member, respectively.

According to yet another aspect of the invention, a method of making a urinary incontinence device is provided. The method includes forming a non-absorbent into core structure and then aligning a generally trapezoidal resilient member adjacent the non-absorbent. The elongated member is then folded upon itself such that its first and second ends are aligned adjacent to one another and the covered elongated member contains at least two folds therebetween. The resilient member extends between the at least two folds. The elongated member is then compressed into an elongated pledget having an insertion end and a trailing end with the resilient member located at least in the insertion end. The resilient member is capable of expanding at least a portion of the pledget to provide a supportive backdrop for a women's urethra when the pledget is inserted into a vagina.

Other aspects of the invention will be apparent to those skilled in the art in view of the appended claims.

DETAILED DESCRIPTION

Figure 11:
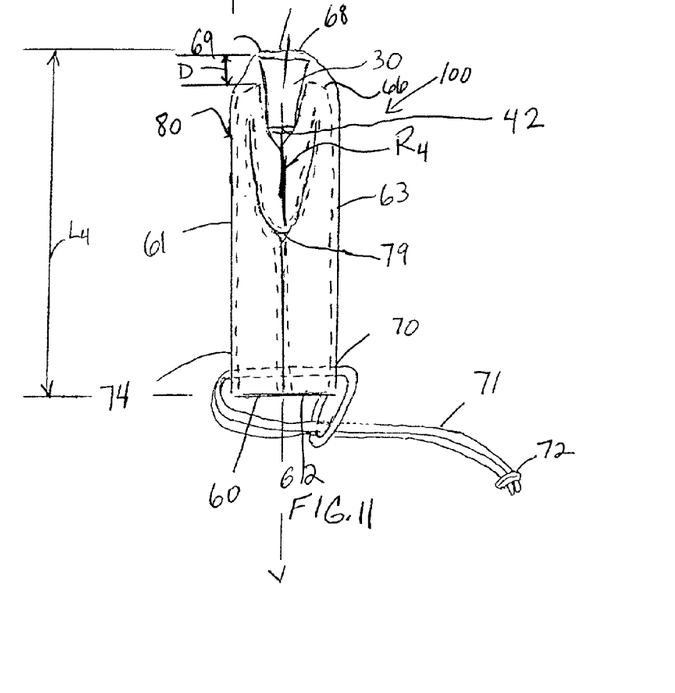
FIG. 11 is a side view of the elongated member of FIG. 10 after it has been compressed into a pledget and has a withdrawal member attached to the first and second ends.

A urinary incontinence device 100, see FIG. 11, is depicted which is designed to be inserted into a vagina and expand so as to relieve or eliminate the involuntary passage of urine through the urethra from the bladder. The expansion of the non-absorbent urinary incontinence device 100 provides a stable backdrop to the musculature and body tissue located at the urethro-vaginal myofascial area compressed upon itself. In addition, the expansion of the urinary incontinence device 100 in the vagina assists the urinary sphincter muscle in maintaining a circular cross-sectional configuration. When this circular cross-sectional configuration is maintained, the sphincter muscle can close properly and decrease the tendency for the involuntary escape of urine due to stress urinary incontinence.

Figure 1:
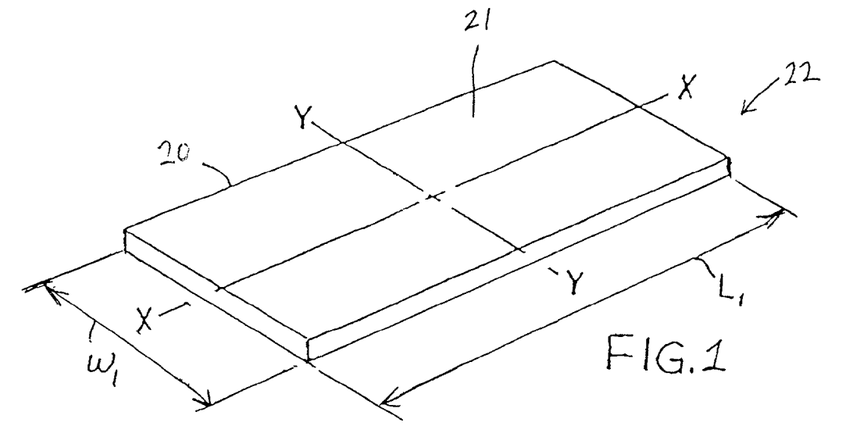
FIG. 1 is a perspective view of an unfolded non-absorbent core structure.
Figure 2:
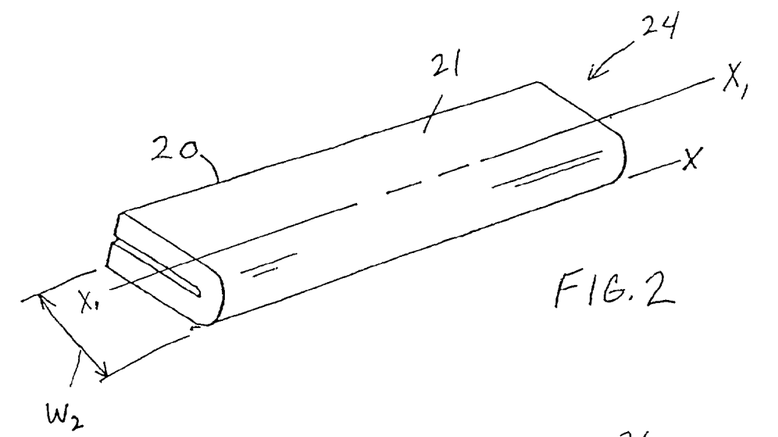
FIG. 2 is a perspective view of the non-absorbent of FIG. 1 after being folded along its longitudinal central axis to form a once folded non-absorbent core structure.
Figure 3:
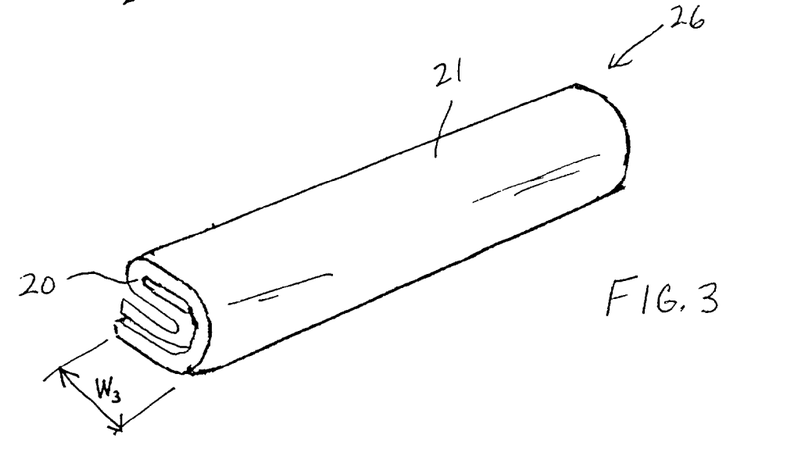
FIG. 3 is a perspective view of the non-absorbent of FIG. 2 after being folded along its longitudinal central axis to form a twice folded non-absorbent core structure.

Referring to FIGS. 1–3, the urinary incontinence device 100 includes a non-absorbent 20. The nonabsorbent 20 has a length $L_1$ and a width $W_1$. The $L_1$ is preferably about 130 mm (5.1 inches) to about 190 mm (7.5 inches). In more preferred embodiments, the length $L_1$ is about 145 mm (5.7 inches) to about 175 mm (6.9 inches). In the most preferred embodiments, the length $L_1$ of the nonabsorbent 20 is about 162 mm (6.4 inches).

The non-absorbent 20 defines the core structure of the urinary incontinence device 100. In serving as the core structure, the non-absorbent 20 can be unfolded into a core structure 22 (FIG. 1), once folded into a core structure 24 (FIG. 2), twice folded into a core structure 26 (FIG. 3), or multiply folded and/or rolled (not shown). The width $W_1$ of the non-absorbent depends upon whether the non-absorbent will be used unfolded, once folded, twice folded, etc. No matter which configuration is used, the width for the top surface 21 as will it be used in the core structure is preferably about 15 mm (0.6 inch) to about 40 mm (1.6 inches). In more preferred embodiments, the width for the top surface 21 as will it be used in the core structure is preferably about 22 mm (0.87 inch) to about 32 mm (1.3 inches). In the most preferred embodiment, the width for the top surface 21 as will it be used in the core structure is preferably about 27.5 mm (1.1 inch). In other words, for the most preferred embodiment of the unfolded non-absorbent 20 as the core structure, $W_1$=27.5 mm. However, where the most preferred embodiment of the twice folded non-absorbent will be used as the core structure, $W_1$=110 mm (4.3 inches), $W_2$=55 mm (2.2 inches), and $W_3$=27.5 mm (1.1 inch).

It should be noted that the above discussion is directed to folding the non-absorbent 20 upon itself to form the core structures. However, the core structures could be formed by rolling, wrapping, bending and/or manipulating one or more of layers of non-absorbent 20 in a known fashion to obtain a cylindrical or elongated core structure.

The non-absorbent 20 is constructed from materials that exhibit little, and preferably, no absorbent characteristics. The non-absorbent 20 differs from a catamenial tampon in that it does not function to absorb body fluid. Instead, the non-absorbent 20 is designed to bridge across the vagina and support the musculature and body tissue located in the urethro-vaginal myofascial area. By doing so, the urethra can be compressed sufficiently to stop the flow of urine and support can be provided to the urinary sphincter muscle so that it can function properly.

For purposes of this invention, a non-absorbent is defined as a material wherein the fibers do not absorb significant quantities of moisture within the fiber itself. It is to be recognized that virtually all materials will absorb some small quantity of moisture. A fiber is considered to be non-absorbent for present purposes if it will intrinsically gain no more than about 6 percent in weight when a bone dry fiber is maintained at 21° C. and at 65 percent relative humidity for 24 hours. Non-absorbent materials include but are not limited to nylons, rayons, spun cellulose, LYCRA®, KEVLAR®, carbon fibers and the like. "LYCRA" and "KELVAR" are trademarks of E.I. DuPont de Nemours & Company which has an office at 1007 Market Street, Wilmington, Del. 19801. One such non-absorbent is a web made from bicomponent fibers which are commercially available from Chisso Corporation having an office at 1411 Broadway, 35th floor, New York, N.Y. Such fibers are sold under the name "Chisso ESC Bicomponent Fiber" and consist of a polypropylene core surrounded by a polyethylene sheath. Fibers that work well have a denier of 3 and are 38 millimeters in length. Other bicomponent fibers made from polypropylene, polyethylene, etc. are commercially available from suppliers such as Exxon and Dow Chemical, as well as from other vendors.

Alternatively, the non-absorbent 20 could be an absorbent material such as a cotton/rayon blend which has been chemically treated with a surfactant to make it non-absorbent. However, materials comprised of truly non-absorbent fibers work best.

Figure 4:
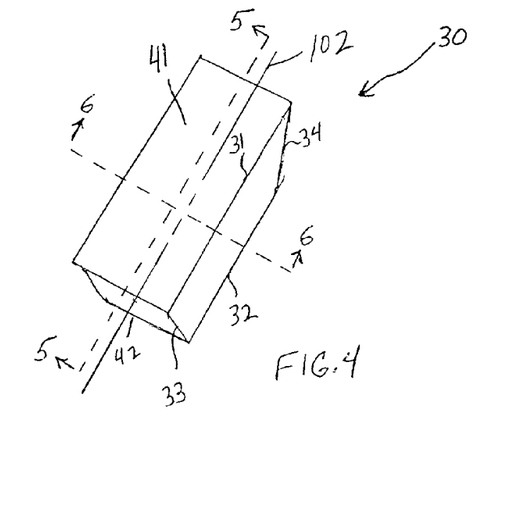
FIG. 4 is a perspective view of the resilient member having a generally trapezoidal profile.
Figure 5A:
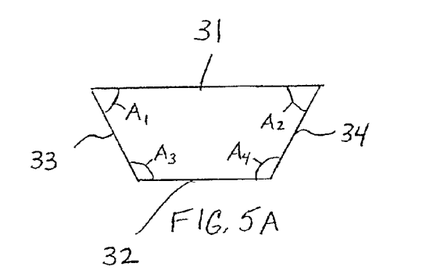
FIG. 5A is a longitudinal cross-sectional view of the trapezoidal profile of the resilient member of FIG. 4 taken along line 5—5.

Referring to FIG. 4, the urinary incontinence device 100 also includes a resilient member 30. The resilient member 30 is elongated and has a generally trapezoidal profile, wherein a pair of the substantially parallel sides 31, 32 of the trapezoid extend generally parallel to the longitudinal axis 102 of the resilient member 30. The resilient member is elongated parallel to the pair of parallel sides 31, 32 of the trapezoidal profile. FIG. 5A shows a longitudinal cross-section of the resilient member 30 of FIG. 4. The trapezoidal profile includes a pair of generally parallel sides 31 and 32 connected by a pair of generally non-parallel sides 33 and 34. The short side 32 of the generally parallel pair of sides is connected to the non-parallel sides 33, 34, by obtuse angles $A_3$ and $A_4$, respectively. The long side 31 of the pair of generally parallel sides is connect to the non-parallel sides 33, 34 by acute angles $A_1$ and $A_2$, respectively. In the preferred embodiments, the longer generally parallel side 31 is preferably about 15 mm (0.6 inch) to about 35 mm (1.4 inches), more preferably about 20 mm (0.79 inch) to about 30 mm 1.2 inches), and most preferably about 25 mm (0.98 inch). The shorter generally parallel side 32 is preferably about 10 mm (0.39 inch) to about 20 mm (0.79 inch); more preferably about 12 mm (0.47 inch) to about 18 mm (0.71 inch); and most preferably about 15 mm (0.59 inch). In the preferred embodiments, the non-parallel sides 33, 34 are about 5 mm (0.2 inch) to about 15 mm (0.59 inch); more preferably about 8 mm (0.31 inch) to about 12 mm (0.47 inch); and most preferably about 10 mm (0.39 inch).

Figure 5B:
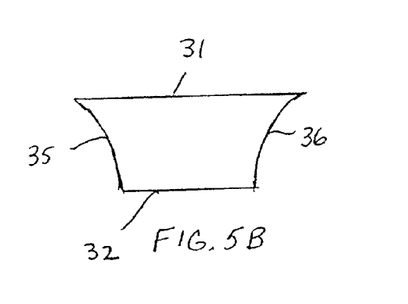
FIG. 5B is a longitudinal cross-sectional view of the trapezoidal profile of an alternate embodiment of the resilient member.
Figure 5C:
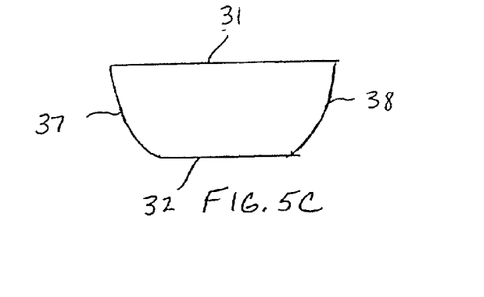
FIG. 5C is a longitudinal cross-sectional view of the trapezoidal profile of an alternate embodiment of resilient member

As used herein, the phrase "generally trapezoidal" includes not only true, quadrilateral, trapezoid shapes (such as in FIG. 5A), but also includes shapes that are nearly trapezoid, such as shapes having one or more rounded sides. For example, in FIG. 5B, the non-parallel sides 35, 36 are curved inwardly. In FIG. 5C, the non-parallel sides 37, 38 are curved outwardly. Both of these shapes are within the scope of the term "generally trapezoidal."

Figure 6A:
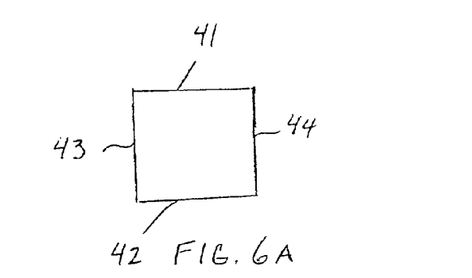
FIG. 6A is a transverse cross-sectional view of the resilient member of FIG. 4 taken along line-6–6.

FIG. 6A illustrates a cross-section of FIG. 4 taken along line 6—6 in direction transverse to longitudinal axis 102. The cross-section is substantially a rectangle having sides 41, 42, 43, and 44. In the preferred embodiment, sides 41 and 42 are about 0.25 inch (6.4 mm) to about 2 inches (51 mm), more preferably about 0.5 inch (12.7 mm) to about 1.25 inches (31.8), and most preferably about 0.75 inch (19 mm). In the preferred embodiment, sides 43 and 44 are about 0.25 inch (6.4 mm) to about 2 inches (51 mm), more preferably about 0.5 inch (12.7 mm) to about 1.25 inches (31.8), and most preferably about 0.75 inch (19 mm).

Figure 6B:
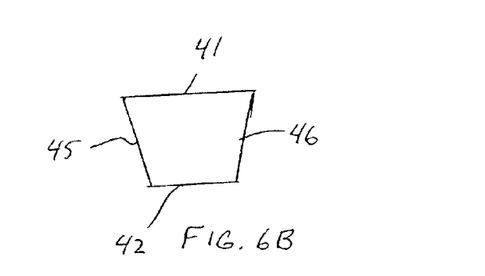
FIG. 6B is a transverse cross-sectional view of an alternate embodiment of the resilient member.

Although a rectangular or square transverse cross-section is preferred, in alternate embodiments, the resilient member 30 has transverse cross-sections having profiles of other quadrilaterals. For example, FIG. 6B shows an alternate transverse cross-section in the shape of a trapezoid having non-parallel sides 45, 46.

The resilient member 30 can be non-absorbent or at least partially absorbent of body fluids. However, there is no functional advantage to making the resilient member 30 absorbent because the urinary incontinence device 100 does not function in a similar manner as does a catamenial tampon. In fact, the urinary incontinence device 100 functions entirely different from an absorbent catamenial tampon.

The resilient member 30 can be a natural or synthetic material which has the ability to quickly recover or return to approximately its original shape and/or dimension. Such change to the resilient member 30 can be created by changes in the intra-abdominal pressure. A resilient material is a material which can return to or resume its original shape or position after being bent, stretched or compressed. The resilient member 30 should also exhibit elasticity and flexibility so that it can be stretched or compressed and still retain the capability of returning to approximately it's original shape.

Two natural materials from which the resilient member 30 can be formed include natural rubber and wool. The number of synthetic materials from which the resilient member 30 can be formed is much greater. Synthetic materials which can be used include polyolefins, polyurethanes, polyethylene oxide (PEO), polyvinyl alcohol (PVA) as well as blends thereof. The resilient member 30 can also be formed from resilient fibers constructed from polyolefin based fibers, polyethylene oxide fibers, hydrophobic rayon fibers and the like, which preferably will have characteristics similar to those of a resilient foam. The resilient fibers may be formed from twisted, curled or chemically cross-linked cellulose fibers or a mixture thereof. Furthermore, the resilient member 30 can be formed from either an open cell or a closed cell foam.

The resilient member 30 can also be made from a wettable foam. An open cell foam which works well and has good resilient properties is commercially available under the trademark ACQUELL®. "ACQUELL" is sold by Sentinel Products Corporation having an office located at 70 Airport Road, Hyannis, Mass. 02601. A polyethylene closed cell foam having good flexibility characteristics also works well. This foam is commercially sold under the trademark VOLARA®. "VOLARA" is available from Voltex, a Division of Sekisui America Corporation having an office located at 100 Shepard Street, Lawrence, Mass. 01843.

The resilient member 30 should also be capable of having what is known as "dry and wet" expansion characteristics. In other words, the resilient member 30 should be made from a material which is capable of expanding or contracting back to or towards its original configuration in a dry state, a wet state or in a semi-dry-wet state. Dry expansion of the urinary incontinence device 100 is beneficial in that the device does not have to be wetted by body fluid before the resilient member 30 is capable of expanding within the vagina.

Figure 7:
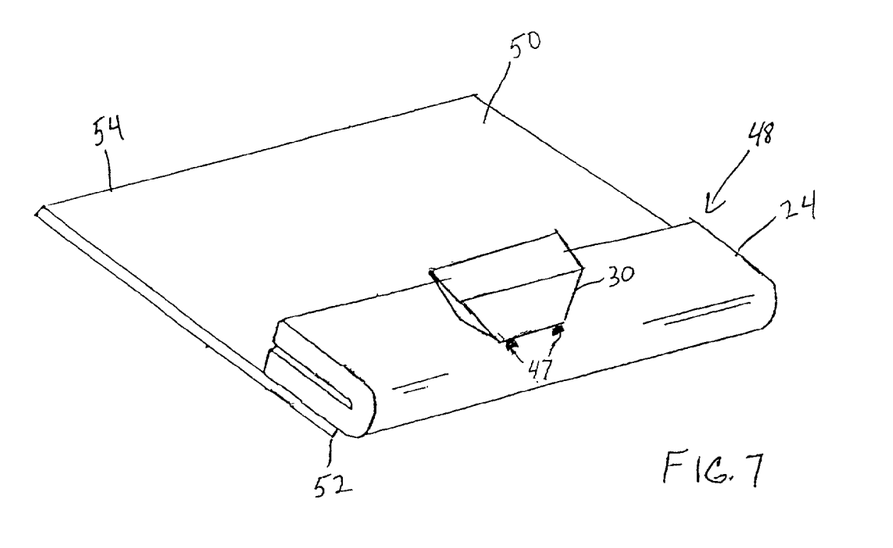
FIG. 7 is a perspective view of the resilient member of FIG. 4 attached to the non-absorbent core structure of FIG. 2 to form a composite elongated member.
Figure 8:
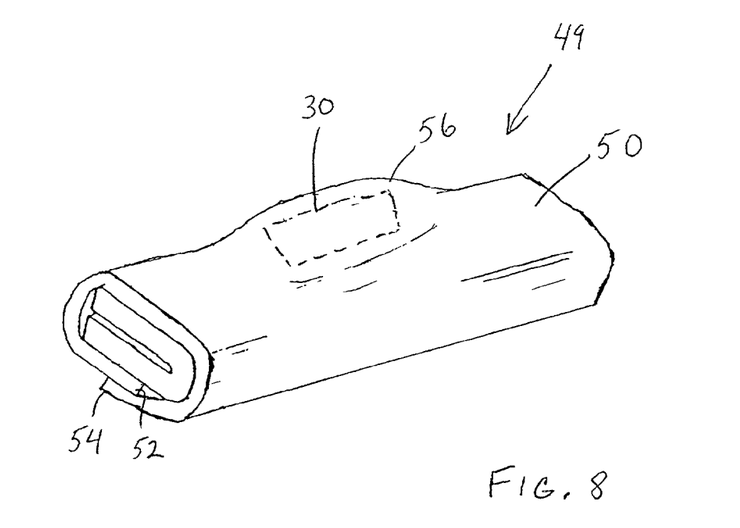
FIG. 8 is a perspective view of a covered elongated member formed from the elongated member of FIG. 7.

Referring now to FIG. 7, the resilient member 30 is centered upon a non-absorbent core structure 24, forming a composite elongated member 48 that may be used to shape the urinary incontinence device 100. The resilient member 30 is preferably attached to the non-absorbent core structure 24 by an adhesive 47, or by a bonding technique known in the art, such as thermo-bonding or ultrasonic-bonding. In alternate embodiments, the resilient member 30 is not attached to the core structure 24, but rather is merely placed upon the core structure. Although the non-absorbent core structure 24 is illustrated in FIGS. 7 and 8, it should be apparent to those skilled in the art that other non-absorbent core structures, such as non-absorbent core structure 22 (FIG. 1) or non-absorbent core structure 26 (FIG. 3), may be used just as well.

Referring again to FIG. 7, the non-absorbent 20 is shown being positioned on a liquid permeable or liquid-impermeable cover 50. The cover 50 is an optional element and need not be present to form the urinary incontinence device 100. However, the cover 50 can provide a smooth outer surface which may or may not be chemically treated to facilitate insertion and/or removal into and out of a vagina. When present, non-absorbent core structure 24 is aligned on the cover such that one edge 52 of the cover 50 is parallel to a surface of the non-absorbent core structure 24 opposite the resilient member 30. The cover 50 is then folded around the non-absorbent core structure 24 and the resilient member 30, forming a covered composite elongated member 49. A raised portion 56 of the cover 50 forms around the area of the cover 50 adjacent the resilient member 30. As shown in FIG. 8, the distal edge 54 of the cover 50 overlaps edge 52 on the surface of the non-absorbent core structure 24 opposite the resilient member 30, and the cover 50 is bonded to itself by heat, pressure, a combination of heat and pressure, or by some other conventional means known to those skilled in the art. If the cover 50 is formed from a material which does not readily bond to itself, an adhesive, glue or other bonding or fastening medium can be used. If desired, the cover 50 may be simply folded over upon itself.

The cover 50 can be either liquid-permeable or liquid-impermeable. When the cover 50 is liquid-impermeable, it serves to block body fluids from contacting the non-absorbent 20. Since the non-absorbent 20 is not designed to absorb any body fluid, it can be liquid-permeable. Liquid permeable materials include woven and nonwoven materials having a porous substrate. Woven materials include textile fabrics which can be made from rayon, cotton, or polyolefins. The polyolefins can be either staple or continuous filaments. The nonwoven materials can include spunbond, bonded carded webs and hydroentangled webs. Spunbond and bonded carded webs are commercially sold by Kimberly-Clark Corporation having an office at 401 N. Lake Street, Neenah, Wis. 54956. Another nonwoven material which can be used as the cover 50 is formed from 100 percent polyester fibers held together by a binder. This material is known as a through-air bonded carded web (TABCW). A particularly preferred TABCW is manufactured by the Kimberly-Clark Corporation of Neenah, Wis.

The cover 50 can also be constructed from a liquid-impermeable material. A good liquid-impermeable material is a micro-embossed, polymeric film, such as polyethylene or polypropylene. Bicomponent films can also be used. A preferred liquid-impermeable material is polyethylene film. The thickness of the cover 50 can range from between about 0.1 mm (0.004 inch) to about 5 mm (0.20 inch), preferably less than about 0.5 mm (0.02 inch), and most preferably, less than about 0.2 mm (0.008 inch).

Figure 9:
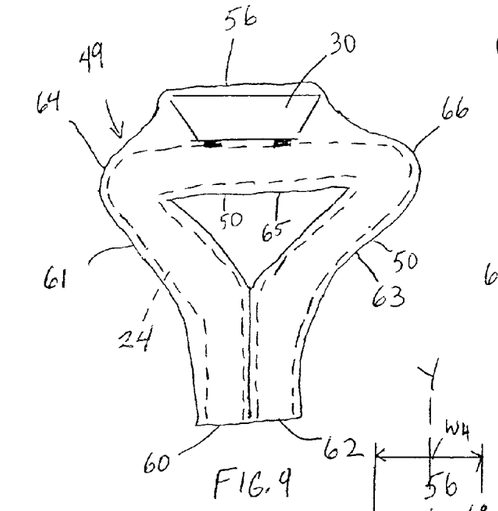
FIG. 9 is a side view of the covered elongated member folded such that the first and second ends are aligned adjacent one another.
Figure 10:
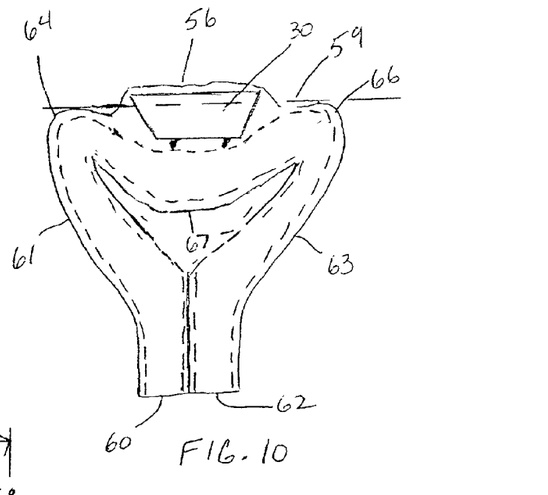
FIG. 10 is a side view of the covered elongated member folded into a generally M-shaped profile.

Referring to FIGS. 9 and 10, the composite elongated member 49 is folded or bent upon itself such that the first and second ends, 60 and 62 respectively, are aligned adjacent to one another and the covered elongated member 49 contains at least two folds 64 and 66 located therebetween. By being aligned "adjacent to one another" it is meant that the first and second ends, 60 and 62 respectively, are positioned side by side, parallel to one another or offset axially or spaced radially apart from one another, or are positioned in some other type of arrangement whereby the first and second ends, 60 and 62 respectively, are close to one another. Preferably, the bonded or open edges of the cover 50 should be positioned to the inside when the first and second ends, 60 and 62 respectively, are aligned adjacent to one another.

The area of the covered elongated member 49 adjacent of the raised portion 56 and the resilient member 30 is then pressed downward towards the first and second ends 60, 62. The elongated member will then contain at least three folds 64, 66, 67 which are located between the first and second ends, 60 and 62 respectively, to give the elongated member 49 a generally M-shaped profile. In the generally M-shaped profile, the elongated member 49 is folded at 64 to form a first portion 61 and is folded a second time at 66 to form a second portion 63 and a third portion 65. The first and second portions, 61 and 63 respectively, preferably have approximately the same length, although their lengths can differ if desired. It is also possible to form the first, second and third portions 61, 63, 65 to have approximately the same length. For example, if the elongated member 49 has a length of about 6 inches (about 152 mm), each of the portions 61, 63, and 65 can have a length of approximately 2 inches (about 51 mm).

Referring to FIG. 11, the composite elongated member 49 is compressed into a pledget 80 having an insertion end 68 and a trailing end 74. The pledget 80 can have any desired shape but preferably, it will have a generally cylindrical shape with a circular cross-sectional configuration. An alternative profile would be a rectangular cross-sectional configuration. The pledget 80 is an elongated member having a length, $L_4$ and a width $W_4$. When the pledget 80 is round in cross-section, its diameter will be equal to the width dimension $W_4$. The length $L_4$ can range from about 0.4 inches (about 10 mm) to about 4.7 inches (about 120 mm), preferably the length $L_4$ ranges from between about 1.5 inches (about 38 mm) to about 2.5 inches (about 64 mm). Most preferably, the length $L_4$ is about 2 inches (about 51 mm). The width $W_4$ can range from between about 0.2 inches (about 5 mm) to about 2.5 inches (about 64 mm), preferably the width $W_4$ ranges from between about 0.5 inches (about 12.7 mm) to about 2.3 inches (about 60 mm). Most preferably, the width $W_4$ is less than about 1.6 inches (about 40 mm). The pledget 80 also has a dimension $R_4$ which is the distance between the bottom edge 42 of the resilient member 30 and the apex 79 of fold 67. The dimension $R_4$ is preferably about 0.5 inch (12.7 mm) to about 1.5 inches (38.1 mm), more preferably about 0.75 inch (about 19.1 mm) to about 1.25 inches (about 31.8 mm), and most preferably about 1.0 inch (25.4 mm) Preferably, the dimension $R_4$ will be about 1 inch (about 25.4 mm) in length. Another way of stating the length of the dimension $R_4$ is to say that it should have a length which is equal to at least about 25 percent of the length $L_4$ of the pledget 80. This length will be sufficient to insure that the pledget 80 can laterally expand outward and provide pressure against the interior walls of the vagina.

Preferably, the elongated member 49 is folded at the third fold 67 such that a top portion of the resilient member 30 extends a distance D out of a plane 59 formed by the first and second folds 64 and 66. D is preferably about 0.05 inch (1.27 mm) to about 0.5 inch (12.7 mm), more preferably about 0.125 (3.2 mm) to about 0.375 inch (9.5 mm), most preferably about 0.25 inch (6.4 mm). This positioning of the resilient member 30 defines a "soft-tip" for the urinary incontinence device 100 which makes insertion more comfortable, as more fully described below. In alternate embodiments, the elongated member 49 is folded more sharply at third fold 67 such that the entire resilient member is below the plane 59, as seen in FIG. 10, formed by the first and third folds 64 and 66.

Still referring to FIG. 11, the insertion end 68 of the pledget 80 is designed to be the first part of the pledget 80 which enters the vaginal cavity. It should be noted that, while in use, the pledget 80 will be entirely positioned within the vagina. The insertion end 68 preferably has a soft tip 69 formed by the extension of the resilient member 30 beyond the plane 59. Because the elongated member 49 has a generally M-shaped profile, the insertion end 68 can contain an equal amount and, preferably, a greater amount of non-absorbent material than the trailing end 74. Even though a greater amount of non-absorbent 20 maybe present at the insertion end 68, the outside diameter of the insertion end 68 should be equal to the outside diameter of the trailing end 74. The amount of non-absorbent material in the insertion end 68 will have to be densified to a greater extent than the non-absorbent material making up the trailing end 74. By having a greater amount of non-absorbent 20 present at the insertion end 68, the urinary incontinence device 100 is better able to expand and support the musculature and the body tissue located adjacent to the urethra and cause it to be compressed. This will eliminate the involuntary escape of urine through the urethra.

When the pledget 80 is formed, the resilient member 30, the non-absorbent 20 and the cover 50, if present, are all compressed. The pledget 80 can be compressed radially and lengthwise or it can be compressed only in the radial direction. The compression step should not detrimentally effect the function of the resilient member 30. In other words, the resilient member 30 has to be capable of expanding outward towards or to its original configuration once the urinary incontinence device 100 is inserted into a vagina. The resilient member 30 must be capable of expanding at least a portion of the pledget 80 to provide support for a urethra when properly inserted into a vagina.

Still referring to FIG. 11, the compressed pledget 80 is pierced at its trailing end 74 to form an aperture or opening 70 which extends completely through the first and second portions, 61 and 63 respectively. The aperture 70 can be formed perpendicular to the central longitudinal axis Y—Y or at an angle thereto. Preferably, the aperture 70 is spaced a short distance from the first and second ends, 60 and 62 respectively. The aperture 70 can be located a distance of from between about 0.1 inches (about 2.5 mm) to about 0.5 inches (about 12.7 mm) from the first and second ends, 60 and 62 respectively. Most preferably, the aperture 70 is located about 0.25 inches (about 6.4 mm) from each of the first and second ends, 60 and 62 respectively. The aperture 70 is designed to allow a withdrawal member 71 to be looped therethrough and be secured to the pledget 80. The withdrawal member 71 will assist in removing the urinary incontinence device 100 from a vagina. The withdrawal member 71 is attached to the non-absorbent 20, and preferably, to the first and second ends 60 and 62, respectively, of the elongated member 49. The aperture 70 can be formed with a needle, an awl or some other type of piercing device known to those skilled in the art. The withdrawal member 71 is threaded through the aperture 70 and looped upon itself so as to cinch it secure to the non-absorbent 20. The free ends of the withdrawal member 71 are then tied in a knot 72 to assure that the withdrawal member 71 will not separate from the pledget 80. The knot 52 also serves to prevent fraying of the withdrawal member 71 and to provide a place or point where a woman can grasp the withdrawal member 71 when she is ready to remove the urinary incontinence device 100 from her vagina.

It should be noted that the withdrawal member 71 holds the first and second ends, 60 and 62 respectively, in direct contact with one another and will limit the amount they can expand while positioned within the vagina. It should also be noted that the withdrawal member 71 can be secured to and/or attached to various areas of the pledget 80 and can pass through one or more of the resilient member 30, the non-absorbent 20, the cover 50, if present, or through all three members, if desired. The aperture 70 can alternatively be formed in the covered elongated member 49 before it is compressed and the withdrawal member 71 can be attached either before the covered elongated member 49 is compressed or after the elongated member 49 is compressed into the pledget 80.

The withdrawal member 71 can be constructed from various types of, strings, threads or ribbons. A thread or ribbon made from 100 percent cotton fibers works well. The withdrawal member 71 should have a length which extends beyond the end of the urinary incontinence device 100 of from between about 2 inches (about 51 mm) to about 8 inches (about 203 mm), preferably, from between about 4 inches (about 102 mm) to about 6 inches (about 152 mm), and most preferably, about 5 inches (about 127 mm). The withdrawal member 71 can be dyed and/or treated with an anti-wicking agent, such as wax, before being secured to the pledget 80. The anti-wicking agent will reduce and hopefully prevent body fluids from wicking along the withdrawal member 71 and contacting the inner surface of a undergarment. A dry, clean withdrawal member 71 is preferred by the user, especially when she goes to remove the urinary incontinence device 100 from her vagina.

Figures 12, 13, 14:
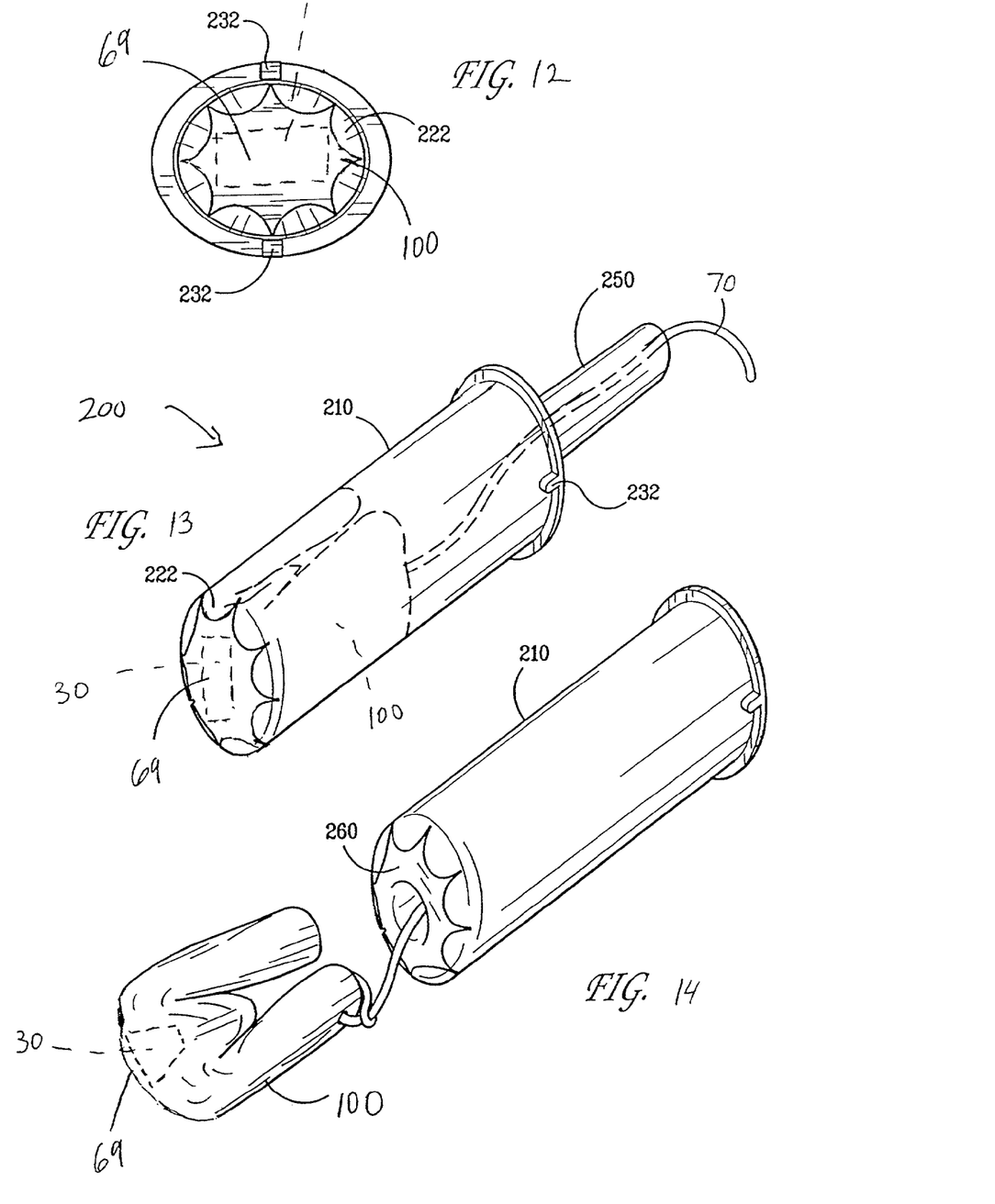
FIGS. 12–14 illustrate the use of the urinary incontinence device with a first preferred applicator.

The insertion of the urinary incontinence device 100 into the human body can be accomplished by use of digital insertion or by use of an applicator. Particularly preferred applicators are disclosed in commonly assigned, co-pending U.S. App. Ser. No. 09/675,458 (659/694), entitled "Incontinence Insert Applicators and a Method of Making the Same," filed Sep. 28, 2000, the entire disclosure of which is incorporated herein by reference. Briefly, as shown in FIGS. 12–14, a preferred applicator 200 has a outer member 210 adapted to house the urinary incontinence device 100, and an inner member 250 adapted to discharge the urinary incontinence device 100 from the outer member. The outer member 210 preferably has an elliptical cross-section at least at its leading, vaginal insertion end, and has one or more orientation indicators 232 to help the user orientate the urinary incontinence device 100 within the vagina. The outer member 210 also includes petals 222 to help soften the insertion process.

As shown in FIGS. 12–14, the urinary incontinence device 100 includes a soft-tip 69 which leads the urinary incontinence device 100 when the device is inserted in into the vagina. The soft tip 69 facilitates the insertion by making it more comfortable to the user by reducing trauma to the vaginal epithelium during insertion. Furthermore, during removal of the device, the generally trapezoidal profile of the resilient member 30 allows it to collapse inwardly upon itself as the insert is then drawn down the vagina. Both of these functions are especially important since the incontinence insert is used primarily inter-menstrually when only a minimal amount of bodily fluid is available to act as natural lubricant.

Figures 15, 16, 17:
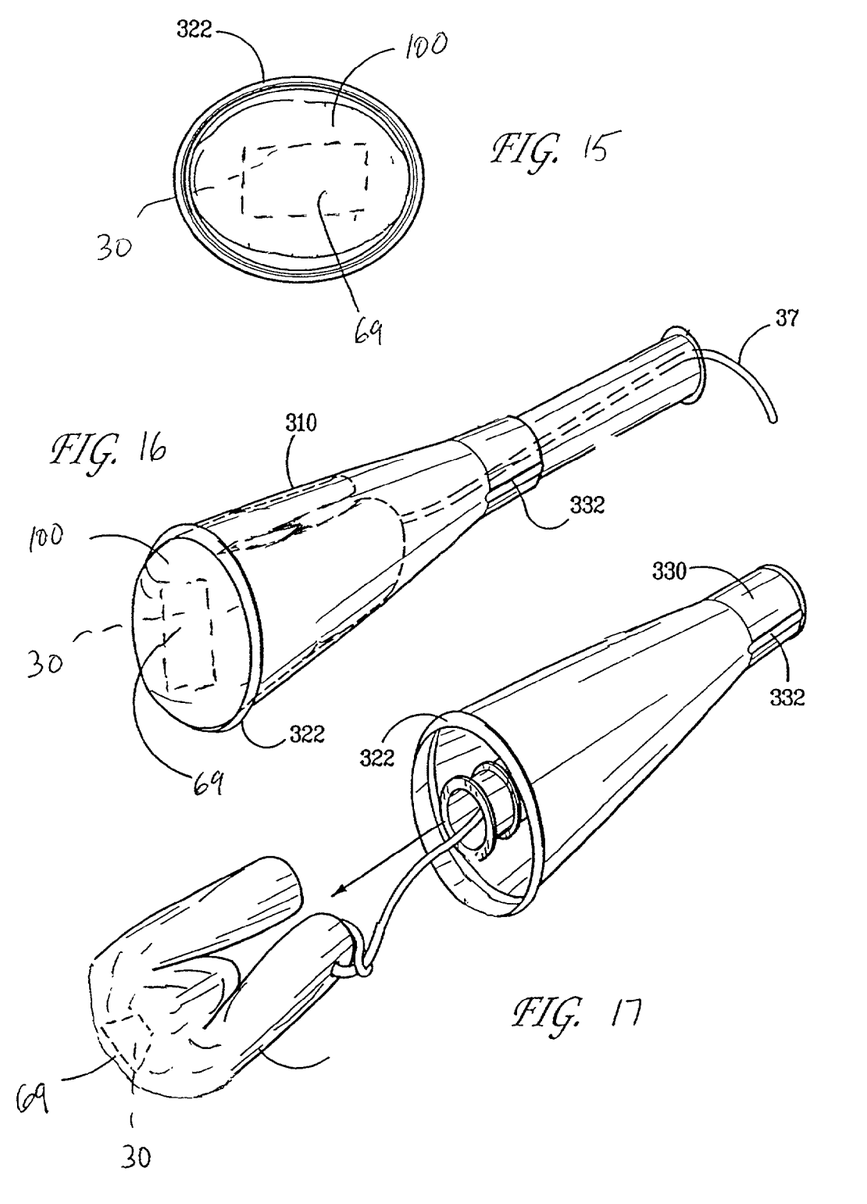
FIGS. 15–17 illustrate the use of the urinary incontinence device with a second preferred applicator.

The soft tip 69 is especially useful with the applicator 300 of FIGS. 15–17. The applicator 300 includes an outer member 310 adapted to house the urinary incontinence device 100, and an inner member 350 adapted to discharge the urinary incontinence device 100 from the outer member 310. The outer member 310 has an elliptical cross-section and orientation indicators 332. Unlike the applicator of FIGS. 12–14, the applicator 300 is petal-less. However, the outer member 310 is cone-shaped, and is designed such that the urinary incontinence device 100 extends out of an exit portion 322 of the outer member 310. Accordingly, the soft tip 69 provides not only a soft leading end for the urinary incontinence device 100, but for the applicator 300 as well.

Figure 18:
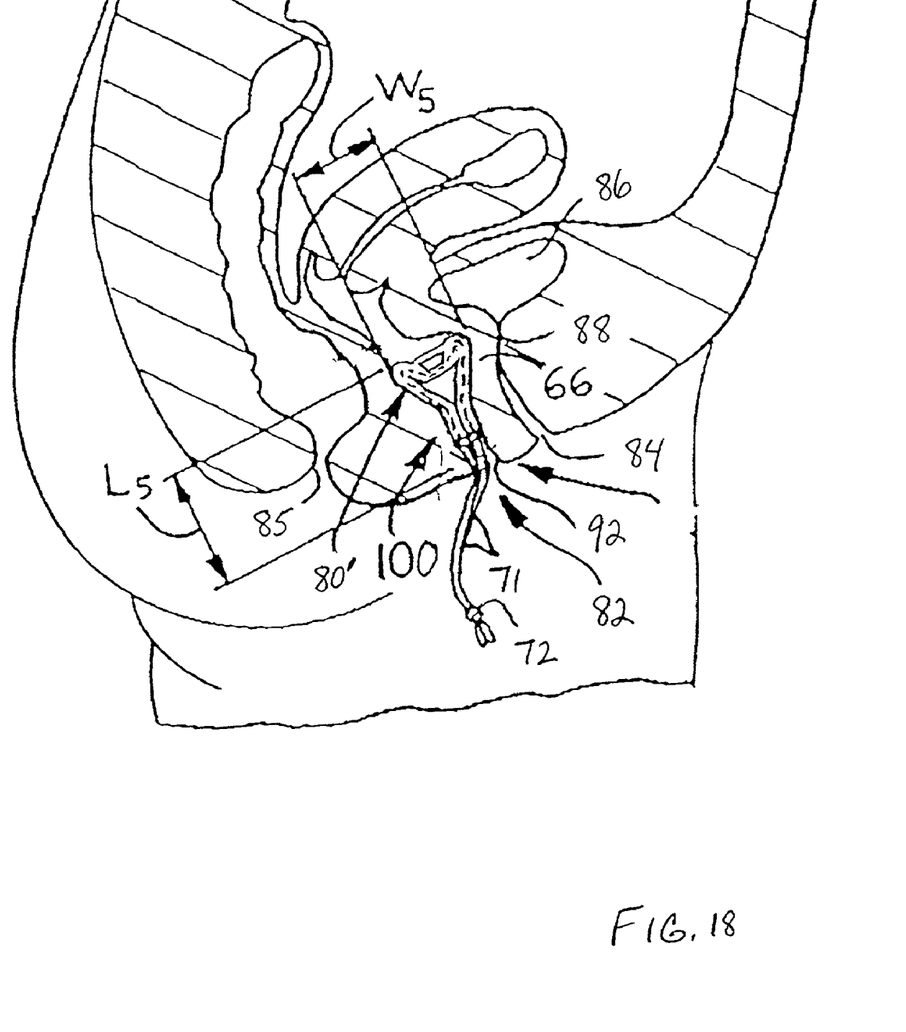
FIG. 18 is a mid-sagittal section of a female human torso showing the urinary incontinence device positioned in the vagina and expanded to provide support for the musculature and tissue near the urethro-vaginal myofascial region and the urethra.

Referring to FIG. 18, the compressed pledget 80 is depicted having been inserted into a vagina 82 and is shown in an expanded state 80'. The expanded pledget 80' has a length $L_5$ and a diameter or width $W_5$. The expanded pledget 80' also has a generally triangular shape which is closed at the bottom or trailing end 74 by the attachment of the withdrawal member 71. While within the vaginal cavity 82, the resilient member 30 will expand thereby causing the first and third portions, 61 and 63 respectively, to spring or expand outward and spread across the vaginal opening. The urinary incontinence device 100 should be positioned below the cervix. The resilient, elastic and flexible characteristics of the resilient member 30 enables the pledget 80 to recover quickly from its compressed and deformed shape. This allows the urinary incontinence device 100 to intimately contact and conform more ideally to the space within the vaginal walls and press against the inside walls and convolutions of a vagina 82.

The urethra 84 is located adjacent to and anterior to the vagina 82. The anus 85 is located on the posterior side of the vagina 82. The urethra 84 is a conduit for removing urine which has accumulated in the bladder 86 to an external orifice located at the lower end of the urethra 84. A urinary sphincter muscle 88 is situated at the upper portion of the urethra 84 adjacent to the bottom surface of the bladder 86. The sphincter muscle 88 operates to prevent the involuntary loss of urine. However, with age the pelvic floor muscles begin to sag and the cross-sectional configuration of the sphincter muscle can change from a circular profile to a non-circular profile. Such a change increases the likelihood that a woman will experience involuntary urine loss.

Between the vagina 82 and the urethra 84 is the urethro-vaginal myofascial area 90. This area 90 is made up of musculature and body tissue and the body tissue is extremely pliable. The vagina 82 contains a plurality of rugosities (not shown) which line its inside walls 92. The rugosities consist of wrinkles or creases in the body tissue which allows for expansion and contraction of the side walls 92 of the vagina 82.

Comparing the compressed pledget 80, shown in FIG. 11, to the expanded pledget 80', shown in FIG. 18, one will quickly recognize that the width $W_5$ of the expanded pledget 80' is much greater than the width $W_4$ of the compressed pledget 80. However, the length $L_5$ of the expanded pledget 80' is approximately equal to the length $L_4$ of the compressed pledget 80. Preferably, the length $L_5$ of the expanded pledget 80' will be slightly larger than the length $L_4$ of the compressed pledget 80. This distance will not change substantially once the urinary incontinence device 100 is inserted into the vagina 82. As the pledget 80 expands by the action of the resilient member 30, to the expanded state 80', the expanded pledget 80' will apply pressure against the body tissue in the urethro-vaginal myofascial area 90. This action will provide a stable backdrop to allow the urethra 84 to become compressed when intra-abdominal pressure increases. In other words, a part of the urethra 84 which is about 1.5 inches (about 38 mm) long and through which urine flows, will be compressed or pinched upon itself thereby preventing the urine from passing through. In addition, support will be provided to the region near the sphincter muscle 88 so that it has a higher tendency to maintain a circular cross-sectional configuration and operate properly. One or both of these actions will reduce and/or prevent involuntary urine loss due to stress urinary incontinence.

METHOD

Figure 19:
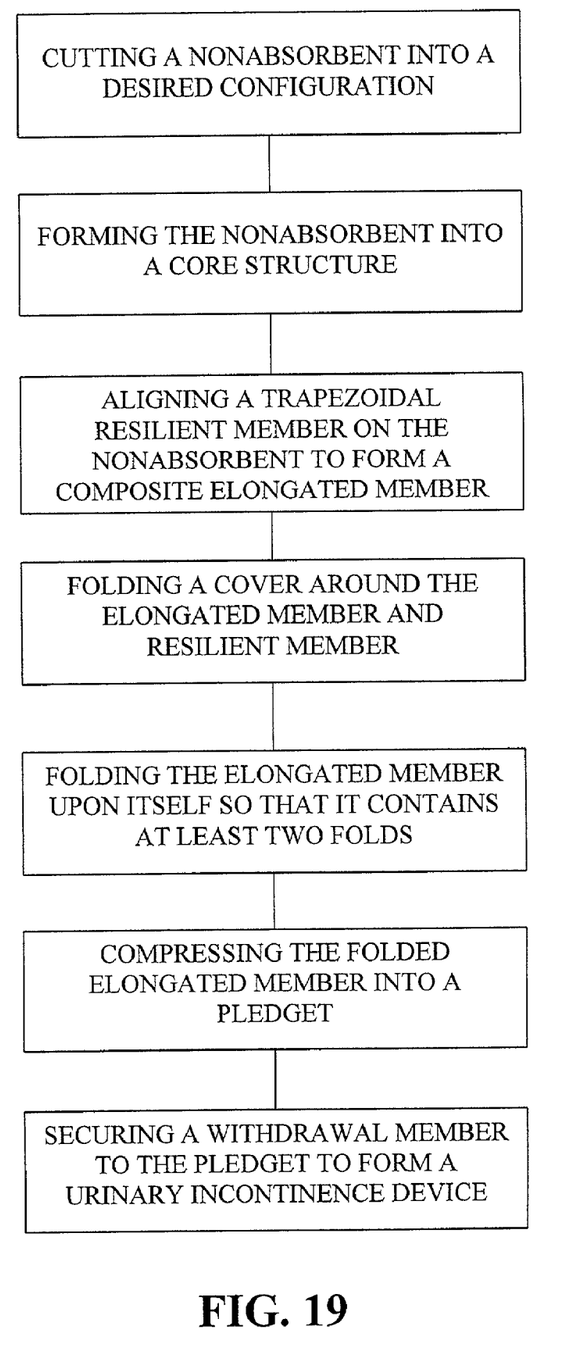
FIG. 19 is a flow diagram of a method of forming a urinary incontinence device.

The method of forming the urinary incontinence device 100 will now be explained with reference to the flow diagrams shown in FIG. 19. The method includes the steps of forming or cutting a non-absorbent 20 into a desired geometrical shape. A preferred shape for the non-absorbent 20 is a rectangle although many other shapes will work. The non-absorbent 20 will have a desired length, width and thickness. Then non-absorbent 20 may be used unfolded as a core structure 22, or may be once folded or twice folded to form core structures 24 and 26, respectively. A resilient member 30 having a generally trapezoidal shaped profile is positioned and centered on or adjacent to one surface of the non-absorbent core structure to form an elongated member.

The non-absorbent 20 can be positioned on a cover material 50 such that the cover 50 is located adjacent to one surface of the non-absorbent 20 and the resilient member 30 is located adjacent to an opposite surface of the non-absorbent 20. The cover 50 is an optional feature and need not be present to make a useful urinary incontinence device 100. The non-absorbent 20, along with the cover 50 are then folded around the resilient member 30. As depicted in FIG. 8, the cover member 50 overlaps itself on a surface of the non-absorbent core structure opposite the resilient member.

It should be noted that the different materials forming the resilient member 30, the non-absorbent 20 and the cover 50 can be folded one or more times to obtain a predetermined diameter or cross-sectional configuration. Furthermore, the materials can be rolled, wrapped, bent or otherwise manipulated to arrange them into a covered elongated member 49.

Once a covered elongated member 49 is formed, it is folded or bent at two or more locations along the length of the elongated member 49 to arrive at a generally triangular profile when viewed perpendicular to the folds. Preferably, the elongated member 49 is folded such that it contains three folds and acquires a generally M-shape profile. Preferably, a portion of the resilient member 30 extends past a plane 59 formed by the first and second folds 64, 66, respectively. An example of the generally M-shaped profile is depicted in FIG. 10. The location or position of the folds 64, 66, and 67 can vary but one preferred embodiment is depicted in FIG. 10.

After the covered elongated member 49 has been folded into a generally triangular or M-shape profile, it is compressed radially into a pledget 80, as depicted in FIG. 11. The elongated member 49 can be compressed only in the radial direction or it can be compressed both axially and radially. Since the pledget 80 contains more material at the insertion end 68 than at the trailing end 74, the insertion end 68 will be denser since the pledget 80 has the same diameter or cross-sectional area throughout its entire length. This added material at the insertion end 68 will assure that as the pledget 80 opens and expands, once it is inserted into a vagina, that it will provide a stable backdrop for the urethra and be able to provide the required pressure against the neighboring body tissue located in the urethro-vaginal myofascial area so as to restrict the involuntary flow of urine through the urethra.

The compressed pledget 80 can then have a hole or aperture 70 formed through its trailing end 74 for receiving a withdrawal member 71. The aperture 70 can be formed with a needle, an awl or some other mechanical, electrical, chemical, hydraulic or pneumatic means. The aperture 70 should be aligned parallel to the first and second ends, 60 and 62 respectively, of the elongated member 49 and be sufficiently spaced apart from the ends 60 and 62 to insure that as one pulls on the withdrawal member 71 that it will not tear through the material and be separated from the pledget 80. The withdrawal member 71 can be inserted through the aperture 70 and be looped upon itself to cinch it tight against the pledget 80. The pair of free ends of the withdrawal member 71 can then be tied in a knot 72 for added assurance that the withdrawal member 71 will not separate from the pledget 80.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

What is claimed is:

1. A urinary incontinence device comprising:
a resilient member having a generally trapezoidal shape; and
a non-absorbent core structure having a first end portion and a second end portion, said core structure being folded upon itself such that said first and second end portions are aligned substantially parallel to one another and said core structure contains at least two folds therebetween to form a generally M-shaped profile; said at least two folds comprising a first fold adjacent said first end portion and a second fold adjacent said second end portion;
said resilient member in contact with said core structure and positioned between said first fold and said second fold.

2. The urinary incontinence device of claim 1, wherein said resilient member is attached with said core structure between said first and second folds to form a composite elongated member.

3. The urinary incontinence device of claim 2, wherein said composite elongated member is folded to form a multi-layer core structure before attaching said resilient member.

4. The urinary incontinence device of claim 2, wherein said composite elongated member is compressed to form a pledget capable of expanding to provide a supportive backdrop for a urethra when inserted into a vagina.

5. The urinary incontinence device of claim 2, further comprising a cover for said elongated member.

6. The urinary incontinence device of claim 4 wherein said resilient member forms a leading tip for insertion of the pledget.

7. The urinary incontinence device of claim 1, further comprising a withdrawal member adapted to remove said urinary incontinence device from the vagina.

8. A urinary incontinence device comprising:
   a resilient member having a profile of two generally parallel sides connected by two generally non-parallel sides, wherein a shorter side of said two generally parallel sides forms an obtuse angle with each of said two generally non-parallel sides;
   an elongated non-absorbent core structure having a first end portion, a second end portion, and a connecting portion between said first end portion and said second end portion; said core structure being folded such that said first and second end portions are aligned substantially parallel; said shorter side of said resilient member in contact with said connecting portion, said connecting portion folded such that a first and second segment of said connecting portion is substantially aligned with and adjacent each of said two generally non-parallel sides of said resilient member, respectively.

9. The urinary incontinence device of claim 8, wherein said resilient member is attached with said core structure between said first and second folds to form a composite elongated member.

10. The urinary incontinence device of claim 9, wherein said non-composite elongated member is folded to form a multi-layer core structure before attaching said resilient member.

11. The urinary incontinence device of claim 9, wherein said composite elongated member is compressed to form a pledget capable of expanding to provide a supportive backdrop for a urethra when inserted into a vagina.

12. The urinary incontinence device of claim 9, further comprising a cover for said elongated member.

13. The urinary incontinence device of claim 8 wherein said resilient member forms a leading tip for insertion of the pledget.

14. The urinary incontinence device of claim 8, further comprising a withdrawal member adapted to remove said urinary incontinence device from the vagina.

15. A method of making a urinary incontinence device, the method comprising:
   a) forming a non-absorbent into a core structure:
   b) aligning a generally trapezoidal resilient member adjacent said non-absorbent to form a composite elongated member having first and second ends;
   c) folding said elongated member upon itself such that said first and second ends are aligned adjacent to one another and said elongated member contains at least two folds therebetween; said resilient member extending between at least said two folds; and
   d) compressing said elongated member into an elongated pledget having an insertion end and a trailing end with said resilient member located at least in said insertion end, whereby said resilient member is capable of expanding at least a portion of said pledget to provide a supportive backdrop for a women's urethra when said pledget is inserted into a vagina.

16. The method of claim 15, wherein a withdrawal member is attached with said trailing end of said pledget.

17. The method of claim 15, further comprising, prior to folding the elongated member upon itself, folding a cover around said composite elongated member and said resilient member to form a covered elongated member.

* * * * *